United States Patent
Katoh et al.

[11] Patent Number: 5,938,671
[45] Date of Patent: Aug. 17, 1999

[54] RECANALIZATION APPARATUS AND DEVICES FOR USE THEREIN AND METHOD

[75] Inventors: Osamu Katoh, Kyoto, Japan; Mir A. Imran, Los Altos Hills, Calif.

[73] Assignee: Reflow, Inc., Menlo Park, Calif.

[21] Appl. No.: 08/970,952

[22] Filed: Nov. 14, 1997

[51] Int. Cl.$^6$ .................................................... A61B 17/22
[52] U.S. Cl. .......................... 606/159; 606/167; 606/185
[58] Field of Search ................................ 606/1, 108, 159, 606/167, 171, 184, 185; 604/272

[56] References Cited

U.S. PATENT DOCUMENTS

| | | | |
|---|---|---|---|
| 5,318,576 | 6/1994 | Plassche et al. | 606/159 |
| 5,520,189 | 5/1996 | Malinowski et al. | 600/585 |
| 5,531,685 | 7/1996 | Hemmer et al. | 604/95 |
| 5,556,406 | 9/1996 | Lary | 606/159 |
| 5,643,298 | 7/1997 | Nordgren et al. | 606/159 |
| 5,681,336 | 10/1997 | Clement et al. | 606/159 |

FOREIGN PATENT DOCUMENTS

| | | | |
|---|---|---|---|
| 0229620 | 7/1987 | European Pat. Off. | 606/159 |

*Primary Examiner*—Glen Dawson
*Attorney, Agent, or Firm*—Harold C. Hohbach; Flehr Hohbach Test Albritton & Herbert LLP

[57] ABSTRACT

Recanalization apparatus for use in crossing a stenosis forming a total occlusion in a vessel formed by a vessel wall, the stenosis having a distal end cap which is convex facing in a proximal direction. The apparatus is comprised of an outer sheath formed of an elongate flexible tubular member having proximal and distal extremities and having a lumen extending from the proximal extremity to the distal extremity. An inner sheath is slidably mounted in the lumen of the outer sheath and is formed of a flexible elongate tubular member having proximal and distal extremities. The distal extremity has a sharpened tip. The inner sheath has a length so that when the sharpened tip is disposed distally of the distal extremity of the outer sheath, the proximal extremity extends proximally of the proximal extremity of the outer sheath. An imaging guide wire is slidably mounted in the lumen of the inner sheath and has proximal and distal extremities. A transducer is mounted on the distal extremity of the imaging guide wire. The he imaging guide wire has a length so that the transducer can extend beyond the distal extremity of the inner sheath with the proximal extremity extending proximally of the proximal extremity of the inner sheath.

9 Claims, 3 Drawing Sheets

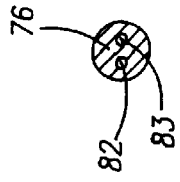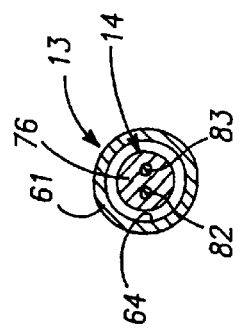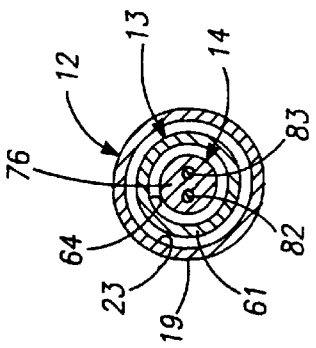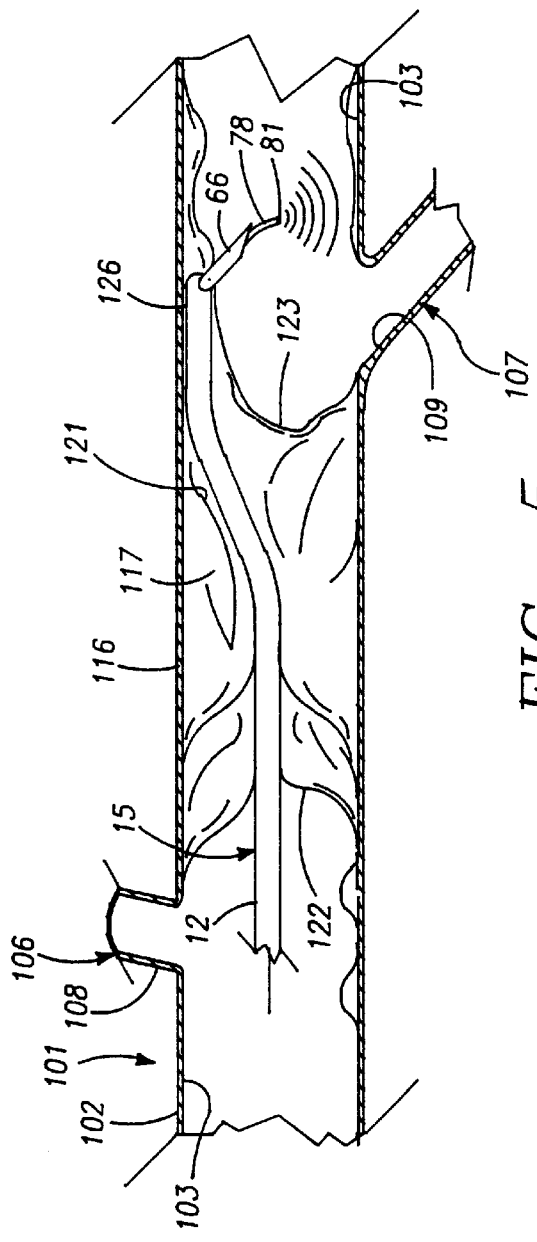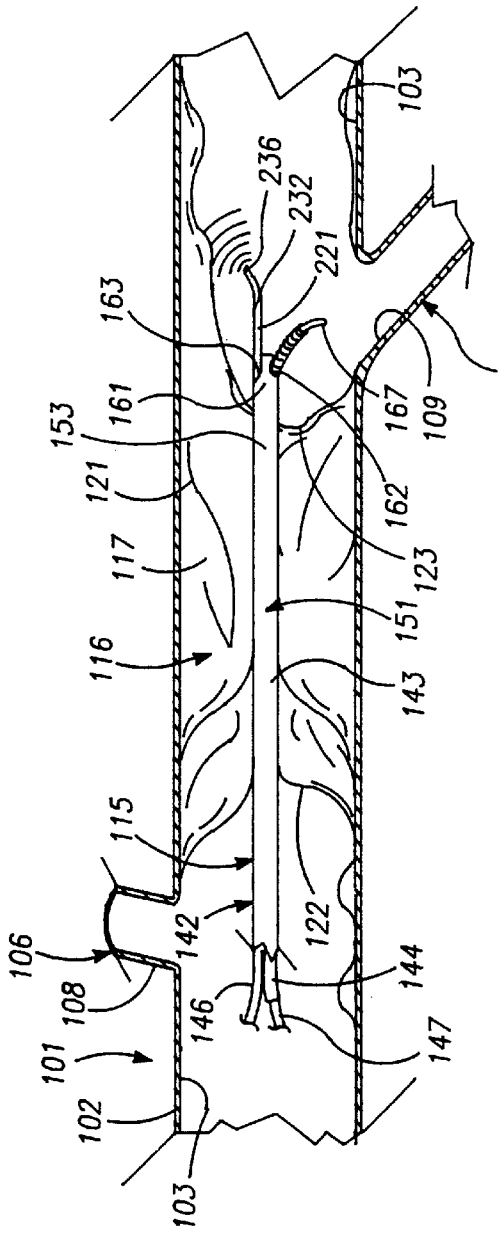

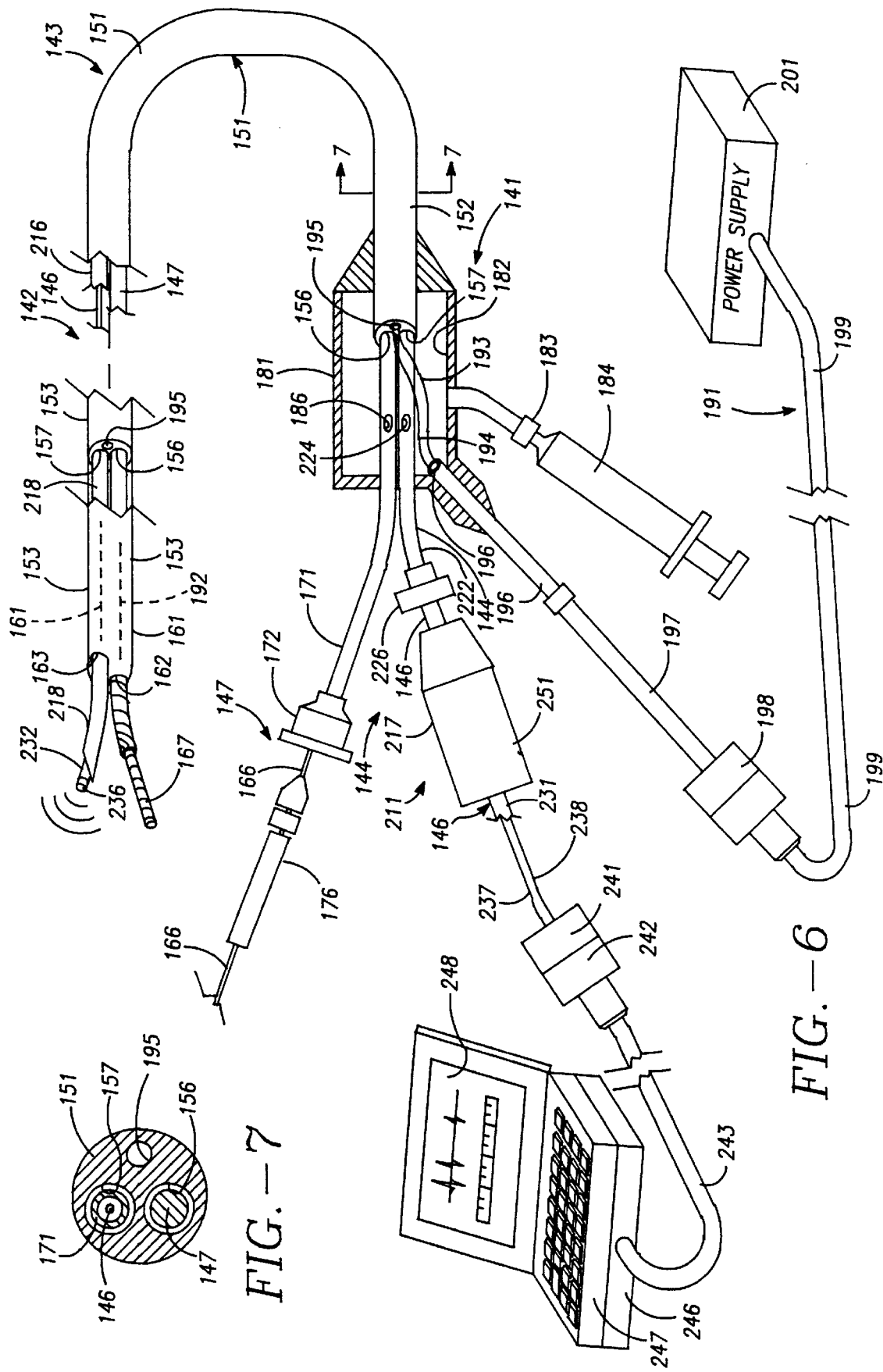

RECANALIZATION APPARATUS AND DEVICES FOR USE THEREIN AND METHOD

This invention relates to a recanalization apparatus and devices for use therein and method for the treatment of total occlusions.

In treating total occlusions, difficulty has been experienced in penetrating the distal fibrous cap of such total occlusions. Such difficulties have been encountered because when it is attempted to push a guide wire through the distal end cap, the guide wire actually follows a false lumen alongside the vessel wall and, after puncturing a vessel wall, rather than puncturing through the fibrous cap and forming a true lumen without puncturing the vessel wall. There is therefore a need for a recanalization apparatus and devices for use therein and a method which overcomes such difficulties and makes it possible to form a true lumen.

In general, it is an object of the present invention to provide a recanalization apparatus and devices for use therein and a method which makes it possible to penetrate a stenosis forming a total occlusion even if there are false lumens in the stenosis.

Another object of the invention is to provide an apparatus, devices and method of the above character which makes it possible to form a passage through a stenosis forming a total occlusion even though a fissure leading toward a vessel wall is followed during the procedure.

Additional objects and features of the invention will appear from the following description in which the preferred embodiments are set forth in detail in conjunction with the accompanying drawings.

FIG. 1 is an illustration of a recanalization apparatus incorporating the present invention and devices for use therein in a coaxial arrangement as used for performing the method of the present invention.

FIGS. 2, 3 and 4 are cross-sectional views taken along the lines 2—2 and 3—3 and 4—4, respectively, of FIG. 1.

FIG. 5 is a cartoon showing the manner in which the recanalization apparatus in FIGS. 1–4 is utilized in performing the method of the present invention.

FIG. 6 is an illustration of a recanalization apparatus incorporating another embodiment of the present invention.

FIG. 7 is a cross-sectional view taken alone the line 7—7 of FIG. 6.

FIG. 8 is a cartoon similar to FIG. 5 showing use of the recanalization apparatus of FIGS. 6–7.

Figure 1:
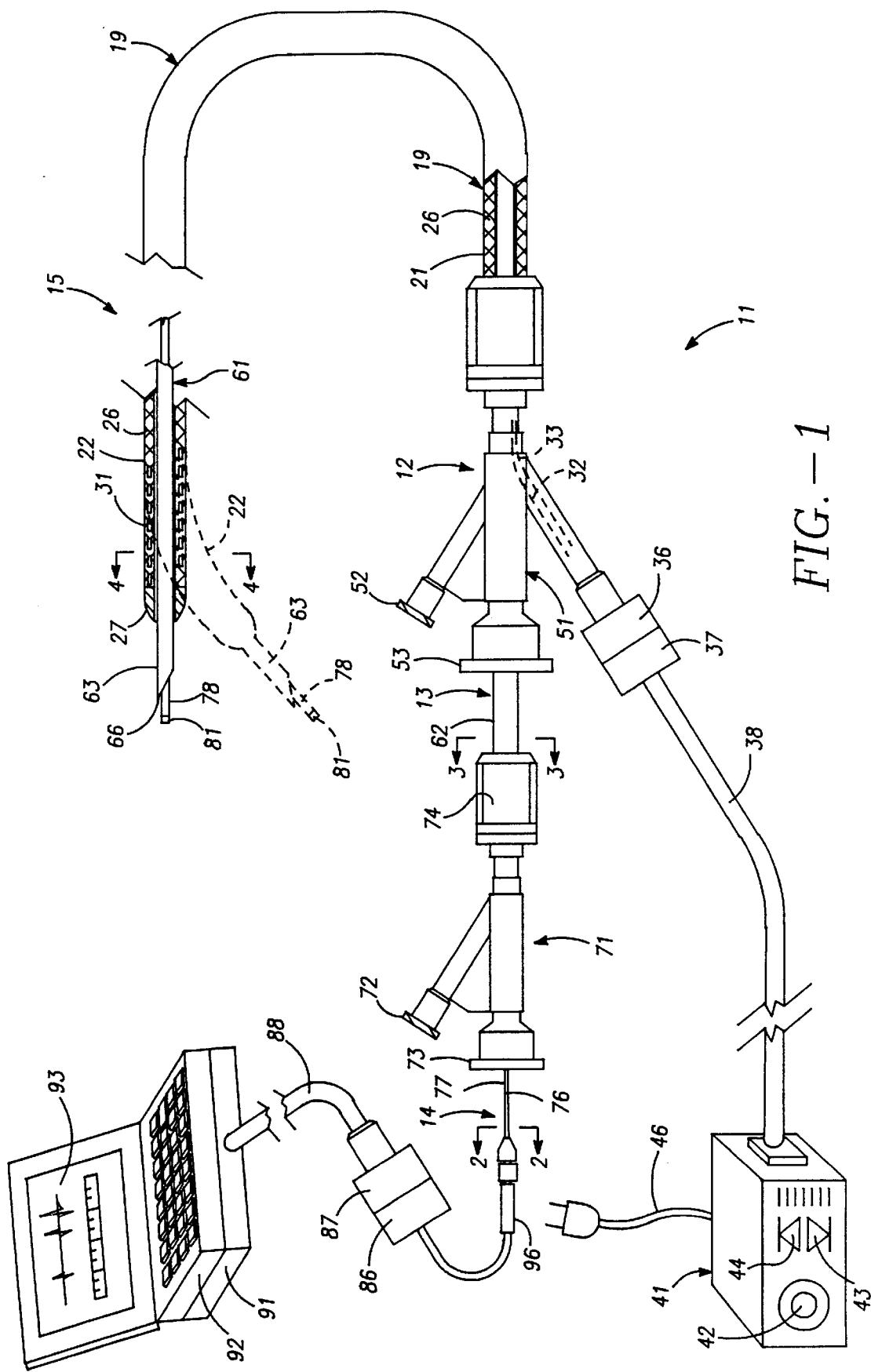

In general, the recanalization apparatus of the present invention is for use in crossing a stenosis forming a total occlusion in a vessel formed by a vessel wall, the stenosis having a distal end cap which is convex facing in a proximal direction. The apparatus is comprised of an outer sheath formed of an elongate flexible tubular member having proximal and distal extremities and having a lumen extending from the proximal extremity to the distal extremity. An inner sheath is slidably mounted in the lumen of the outer sheath and is formed of a flexible elongate tubular member having proximal and distal extremities. The distal extremity has a sharpened tip. The inner sheath has a length so that when the sharpened tip is disposed distally of the distal extremity of the outer sheath, the proximal extremity extends proximally of the proximal extremity of the outer sheath. An imaging guide wire is slidably mounted in the lumen of the inner sheath and has proximal and distal extremities. A transducer is mounted on the distal extremity of the imaging guide wire. The he imaging guide wire has a length so that the transducer can extend beyond the distal extremity of the inner sheath with the proximal extremity extending proximally of the proximal extremity of the inner sheath.

More specifically, the recanalization apparatus and the devices for use therein incorporating the present invention are shown FIG. 1. As shown therein, the recanalization apparatus 11 consists of an outer sheath 12, an inner sheath 13 and an electrical guide wire 14 which as shown are assembled into an assembly 15. It also consists of a power supply 16 for supplying electrical energy to the outer sheath 12 and an ultrasonic power supply 17 for the electrical guide wire 14.

The outer sheath 12 comprises a flexible elongate tubular member 19 having proximal and distal extremities 21 and 22 and a lumen 23 extending therethrough from the proximal extremity 21 to the distal extremity 22. The tubular member 19 can have a suitable length as for example 120–150 cm having a lumen 23 having a size ranging from 0.02" to 0.023" with an outside diameter of 0.035" corresponding to approximately 2.8 French to provide a wall thickness of approximately 0.006". The outer sheath 12 is formed of a suitable material such as plastic and in order to provide kink resistance and torquability, a braid or coil 26 is provided in the plastic material forming the lumen 23 typically extending from the proximal extremity to the distal extremity. A soft tip 27 of low durometer plastic is formed on the distal extremity 22. In accordance with the present invention it is desired that the distal extremity 22 be deflectable under the control of the physician utilizing the recanalization apparatus 11. As disclosed in co-pending application Ser. No. 08/970,911 filed Nov. 14, 1997 this can be accomplished by placing a shape memory member 31 centered in the distal extremity 22 of the outer sheath 12 and can take the form of a helical coil wound from a flat ribbon of a suitable nickel-titanium alloy which has been heat treated and annealed so that it is martensitic at body temperature of 98.6° F. or 37° C. and has a straight shape and when heated above a body temperature becomes austenitic and assumes a predetermined shape of, for example, forming a substantially 90° bend in the coil to thereby yieldably urge the distal extremity 22 to a curved or bent configuration as shown by the dotted lines in FIG. 1. Heat is supplied to the shape memory member 31 in a suitable manner such as by supplying electrical energy to the same by use of conductors 32 and 33 connected at opposite ends of the shape memory member 31. The conductors 32 and 33 extend proximally through the member 31 and are connected into a connector 36 which is mated with another connector 37 connected to a cord 38 and connected to a deflection power supply 41 of a conventional type. The power supply 41 is provided with an on-off switch 42 and up and down switches 43 and 44 for controlling the amount of energy supplied to the shape memory member 31 and thereby controlling the. degree of bending of the distal extremity 22 of the outer sheath 12. The power supply 41 is provided with a power cord 46 for connection to a conventional AC power supply.

A fitting 51 is mounted on the proximal extremity 21 of the tubular member 19 and carries the connector 36. The fitting 51 is provided with a flushing port 52 through which a suitable flushing liquid such as a saline solution can be introduced by suitable means such as a syringe (not shown). The fitting also carries a hemostasis valve assembly 53 through which the inner sheath 13 extends.

The inner sheath 13 consists of a flexible elongate tubular member 61 having proximal and distal extremities 62 and 63 and having a lumen 64 extending therethrough from the proximal extremity 62 to the distal extremity 63. The tubular member 61 is formed of a suitable material such as a plastic or stainless steel or a combination thereof. When formed of plastic, at least the distal extremity 63 should be formed of stainless steel or a nickel-titanium alloy so that it can be provided with a sharp tip 66 at the distal extremity so that the inner sheath 13 can serve as a needle cannula. It should have a length which is greater than the length of the outer sheath 12 so that its distal extremity 63 can extend beyond the soft tip 27 while the proximal extremity 62 is proximal of the hemostasis valve assembly 53 a sufficient distance so that it can be readily grasped by the hand of the physician.

The flexible elongate tubular member 61 is sized so that it can slidably extend through the lumen 23 of the outer sheath 12. Thus by way of example, the flexible elongate tubular member 61 can have a suitable outside diameter as for example 0.02" and a lumen having a diameter of 0.010" to provide a wall thickness of 0.005". It can be seen that it has a sufficient wall thickness to provide the pushability required for slidably moving the flexible elongate tubular member 61 within the outer sheath.

A conventional fitting 71 is mounted on the proximal extremity 62 of the tubular member 61 and is provided with a sidewise extending flush port 72 and a conventional hemostasis value 73 and a rotating joint 74.

The electrical guide wire 14 can be of a conventional type. It typically consists of a flexible elongate tubular member 76 having proximal and distal extremities 77 and 78. As is well known to those skilled in the art, the distal extremity 78 is typically provided with a coil (not shown) to provide additional flexibility for the distal extremity 78 to facilitate guiding of the guide wire 14 through vessels in the human body. An ultrasonic transducer 81 is mounted on the distal extremity 78 and also is of conventional type which operates in the A-mode to propagate forwardly looking wave trains of ultrasonic pulses which are used for ranging purposes with the reflected ultrasonic waves being received by the transducer 81. Electrical energy is supplied to the transducer 81 and is converted to ultrasound waves by the transducer 81. This electrical energy is supplied to and the electrical energy is received from the transducer 81 by conducting wires 82 and 83 connected to the transducer 81 and which extend interiorly of the flexible elongate tubular member 76 to the proximal extremity 77 and are connected to a conventional removable connector 86 which permits rotation of the flexible elongate tubular member 76 with respect to the connector 86 while the connector 86 maintains electrical contact with the wires 82 and 83. The connector 86 is mated with another connector 87 that is connected to a cord 88 which is connected to an ultrasonic power supply 91 having a frequency output ranging from 5–20 Mhz. A notebook-type or lap-type computer 92 interfaces with the power supply 91 for controlling the same and at the same time providing a display of the output on a screen 93.

A torquer 96 of a conventional type is mounted on the proximal extremity 77 of the guide wire 14 and, as is well known to those skilled in the art, is utilized for rotating the guide wire to facilitate advancing the distal extremity of the guide wire 14 through tortuous vessels. The guide wire 14 of the present invention has an outside diameter of 0.009" to 0.010" and has a length ranging from 150–175 cm so that its distal extremity 78 extends out of the distal extremity 63 of the inner sheath 13 while having its proximal extremity 77 accessible outside the human body in which the device is placed to permit manipulation of the proximal extremity 77 and the use of the torquer 96.

Operation and use of the recanalization apparatus 11 of the present invention may now be briefly described as follows in performing a method or procedure for traversing a total occlusion and particularly a chronic total occlusion with the use of the cartoon shown in FIG. 5. An arterial vessel 101 on the wall of the heart in the body of a human being is shown with the vessel 101 having a vessel wall 102 defining a lumen 103 through which blood normally flows. The vessel 101 is provided with side branches 106 and 107 which have walls 108 and 109, respectively, which define branch lumens 111 and 112 in communication with the main lumen 103.

As shown in the cartoon in FIG. 5 let it be assumed that a total occlusion which in fact can be a chronic total occlusion is formed by a stenosis or lesion 116 in the vessel 101 between the branches 106 and 107. Typically such chronic or aged total occlusions are comprised of pre-existing old plaque 117 which typically is fissured. Such pre-existing plaque has a complex structure in which fibrous or calcified tissues are intermingled with loose tissues often having sidewise extending fissures 121 in the same. In addition such pre-existing plaque has proximal and distal fibrous end caps 122 and 123 which develop as fibrous layers of organized thrombus. Typically this progression of the pre-existing plaque 117 continues to the proximal and distal side branches 106 and 107. As shown, the proximal end cap 122 is typically concave when viewed from the proximal direction, whereas the distal end cap 123 is convex when viewed from a proximal direction. In order to treat the total occlusion as shown in FIG. 5, the recanalization apparatus is utilized.

The femoral artery is accessed in a conventional manner. The outer sheath 12, the inner sheath 13 and the electrical guide wire 14 are assembly coaxially into the assembly 15 and can be advanced as an assembly 15 through the femoral artery with the distal extremity 63 of the inner sheath 13 being retracted proximally of the soft tip 27 and similarly the distal extremity 78 of the guide wire 14 being retracted into the distal extremity 63 of the tubular member 61 of the inner sheath 13. The distal extremity 22 of the outer sheath 12 is guided through the vessel of interest by use of the power supply 41 to apply energy to the shape memory member 31 to cause the desired bending of the distal extremity 22. At the same time the physician can apply torque to the proximal extremity 21 of the outer sheath 12 by grasping the proximal extremity 21 extending out of the body to thereby manipulate the distal extremity 22 to cause it to traverse the vessel 101 until it has been advanced into close proximity to the proximal end cap 122. Since the end cap 122 is concave, there will be a tendency for the distal extremity 22 to center in the concave side of the hemispherical end cap 122 so that its longitudinally axis is perpendicular to the face of the end cap 122. The guide wire 14 then can be advanced out of the inner sheath 13 and pushed distally to perforate the proximal end cap 122 while using its ultrasonic ranging capabilities. If this proves to be too difficult for the small diameter guide wire 14, the inner sheath 13 which serves as a needle cannula carrying the sharpened tip 66 can be advanced during the same time that ultrasonic waves are being propagated from the transducer 81 to ascertain the spacing from the end cap and to help ensure that the sharpened tip 66 is advancing through the concave surface of the proximal end cap 122 and not through the wall 102 defining the lumen 103.

As soon as the proximal end cap 122 has been pierced by the sharpened tip 66, the entire assembly 15 can be advanced through the stenosis 116 forming the total occlusion after the sharpened tip 66 and the guide wire 14 therein have been withdrawn proximally of the soft tip 27 of the outer sheath 12. Thereafter, the soft tip 27 is advanced through the pre-existing plaque 117 and into engagement with the distal cap 123 which, because of its convex shape, causes the soft tip 27 to be deflected sideways and enter a fissure 121 in the plaque 117 and thus slip to one side of the distal end cap 123 to create an undesirable false lumen 126. To remedy this situation, let it be assumed that it is necessary to reach the true lumen 103 from the false lumen 126. As this is being accomplished, the advancement of the assembly 15 is monitored by viewing the screen 93 so that deflection of the distal extremity 63 of the outer sheath 12 can be controlled utilizing the power supply 41. During rotation of the outer sheath 12 or alternatively during rotation of the guide wire 14, it is possible to orient the outer sheath 12 as well as the guide wire 14 to ascertain the orientation of the distal extremity 22 of the outer sheath 12. By observing the echoes received from the transducer 81, it is possible to orient the coaxially mounted inner sheath 13 so that its sharpened tip 66 is properly oriented toward the true lumen 103. The proximal extremity 62 of the inner sheath 13 can then be grasped by the physician and pushed to advance the sharpened tip 66 through the outer perimeter of the distal end cap 123 into the true lumen 103 from the false lumen 126. The imaging guide wire 14 is advanced into the true lumen 103. As soon as it has been ascertained that the distal extremity 78 of the imaging guide wire 14 is disposed in the true lumen 103, the outer sheath 12 and the inner sheath 13 can be removed over the proximal extremity 77 of the imaging guide wire by removal of the torquer 96 and removal of the removable connector 86 while leaving the imaging guide wire 14 in place. This can be readily accomplished in a manner well known to those skilled in the art by use of an extension guide wire (not shown). As soon as this has been accomplished, other treatment devices such as a balloon dilatation catheter (not shown) can be advanced over the imaging guide wire 14 by following the imaging guide wire through the stenosis 116 past the distal end cap 123. As soon as the balloon catheter is in place, the imaging guide wire 14 can be removed and in its place, a larger diameter conventional guide wire (not shown), as for example a 0.014" guide wire is inserted. This conventional 0.014" guide wire is advanced so that its distal extremity extends through the balloon catheter and beyond the distal extremity of the balloon catheter and into the lumen 103 beyond the distal end cap 123 of the stenosis 116. Thereafter, the balloon on the balloon catheter can be inflated to compress the plaque 117 forming the stenosis 116 to provide a greatly increased flow passage through the stenosis 116 for establishing a blood flow through the lumen 103. Typical angioplasty procedures can be utilized to obtain the desired size of opening through the stenosis. For example leaving the 0.014" guide wire in place, the balloon catheter mounted thereon can be slidably removed and a balloon catheter having a larger size balloon can be advanced over the guide wire into the stenosis 116 to provide a still larger flow passage through the stenosis. Additionally at the same time if desired, a stent can be deployed into the stenosis 116. Thereafter, the additional catheter and the 0.014" guide wire can be removed in a conventional manner to complete the recanalization procedure.

Another embodiment of a recanalization apparatus incorporating the present invention is shown in FIG. 6. As shown in FIG. 6, the recanalization apparatus consists of a non-coaxial assembly 142 comprised of an outer sheath 143, an inner sheath 144 and an imaging guide wire 146. There is also provided another larger size guide wire 147.

The outer sheath 143 consists of a flexible elongate tubular member 151 having proximal and distal extremities 152 and 153 and has lumens 156 and 157 extending from the proximal extremity 152 to the distal extremity 153. The distal extremity 153 is provided with a soft tip 161 through which the lumens 156 and 157 extend with the lumen 156 extending through an opening 162 which is substantially perpendicular to the longitudinal axis of the outer sheath 143 and with another opening 163 extending at an angle with respect to the longitudinal axis as for example at an angle of approximately 45° as shown in FIG. 6. The tubular member 151 can be of a suitable size as for example 0.039" with the lumens 156 and 157 having a suitable inside diameter as for example 0.016".

The guide wire 147 which is of a conventional type as for example a 0.14" guide wire which has proximal and distal extremities 166 and 167. The distal extremity 167 is typically formed of a coil as shown and is relatively flexible. The proximal extremity 166 extends from the sheath 143 through a tubular member 171 having a conventional hemostasis valve assembly 172 mounted thereon. A torquer 176 of a conventional type is mounted on the proximal extremity 166 of the guide wire 147 for torquing of the guide wire 147 as the guide wire 147 is advanced as hereinafter described.

A fitting 181 is mounted on the proximal extremity 152 of the outer sheath 151 and provides an enclosed space 182 which is adapted to receive a flushing solution as for example a saline solution from a flush port 183 which is adapted to be connected to a conventional syringe 184 for supplying the flushing liquid into the enclosed space 182. The tubular member 171 is provided with an opening 186 therein which is in communication with the interior of the tubular member 171 and which is in communication with the lumen 156 so that a flushing solution can be discharged through the opening 162 into a vessel which is being treated.

If desired and as shown in FIG. 6, means is provided for causing bending of the distal extremity 153 of the outer sheath 143. This means 191 consists of a cylindrical shape memory member 192 of the type hereinbefore described embedded within the distal extremity which is connected to conductors 193 and 194 which extend through a lumen 195 to the proximal extremity 152 of the tubular member 151. The conductors 193 and 194 are connected into a cable 196 which extends through the fitting 181 and are connected to a connector 197 which is connected to another mating connector 198. The connector 198 is connected to a cord 199 which is connected to a power supply 201 of the type hereinbefore described as power supply 41. As hereinbefore described, by supplying energy to the shape memory member 192 from the power supply 201, the distal extremity can be bent in the manner hereinbefore described with the embodiment of the invention shown in FIG. 1.

A subassembly 211 consisting of the inner sheath 144 and imaging guide wire 146 is slidably mounted in the other lumen 157 in the outer sheath 143. The inner sheath 144 consists of a flexible elongate tubular member 216 having proximal and distal extremities 217 and 218 with a lumen 219 extending from the proximal extremity 217 to the distal extremity 218. The flexible elongate tubular member 216 can be formed of a suitable material such as plastic or stainless steel. If formed of plastic, at least a portion of the distal extremity should be formed of stainless steel to provide a sharpened tip 221 as shown in FIG. 6. The proximal extremity 217 extends through a tubular member 222 extending through the fitting 181 and coupled to establish communication with the lumen 157. The tubular member 222 is provided with an opening 223 through which a flushing liquid in the chamber 182 can pass into the lumen 219. A hemostasis valve assembly 226 is mounted on the proximal extremity of the tubular member 222 and is adapted to form a liquid-tight seal with respect to the inner sheath 144 and the coaxially mounted imaging guide wire 146 extending therethrough.

The imaging guide wire 146 is provided with proximal and distal extremities 231 and 232. An ultrasonic transducer 236 of the type hereinbefore described is mounted on the distal extremity 232 and is provided for propagating ultrasound waves distally of the transducer 236. Conductors (not shown) are connected to the transducer 236 extend interiorly of the guide wire 146 and are connected to a conventional removable connector 241 which is connected to another mating connector 242. Connector 242 is connected by a cord 243 to an ultrasonic power supply 246 of the type hereinbefore described which is controlled by a laptop computer 247 mounted thereon which is provided with a screen 248. A torquer 251 of a conventional type is mounted on the proximal extremity 231 and is used for rotating the imaging guide wire 146.

The inner sheath or cannula 144 can have a suitable outside diameter as for example 0.014" to 0.015" and the imaging guide wire 146 can have a suitable outside diameter as for example 0.010" to 0.011".

Operation and use of the canalization apparatus 141 shown in FIGS. 6 and 7 may be briefly described as follows. Let it be assumed that a method or procedure for traversing a total occlusion and particularly a chronic total occlusion is to be performed. In many respects, the method or procedure utilized is similar to that utilized with the recanalization apparatus 11 hereinbefore described. This operation and use also can be described in conjunction with the cartoon shown in FIG. 8. The femoral artery of the patient is accessed in a conventional manner and then the entire assembly 142 can be advanced into the arterial vessel with the inner sheath 144 and the imaging guide wire 146 retracted within the opening 163. The larger guide wire 147 which is part of the assembly can either have been placed first in the arterial vessel by advancing it into the desired position and thereafter introducing the outer sheath over the guide wire 147 by inserting the proximal extremity of the guide wire 146 into the opening 162 and then progressively advancing the outer sheath 143 over the guide wire until the sheath 143 has reached the proximal end cap 122 of the stenosis 116 in the lumen 103 of the arterial vessel 101. During the procedure, when advancing the distal extremity 153 to the desired position it may be necessary to bend the distal extremity 153 while the proximal extremity 152 is being rotated by hand to cause the distal extremity to be advanced so that it is adjacent the proximal end cap 122. If the large guide wire 147 has been able to penetrate the proximal fibrous cap 122 and advance therethrough and through the plaque 117 and then is deflected by the distal fibrous cap 123 into a false lumen 126 as hereinbefore described, the distal extremity 161 of the outer sheath 143 can be advanced over the guide wire through the proximal fibrous cap 122, then through the plaque 117 and then through the false lumen 126. During the time this is occurring, the imaging guide wire 146 can be advanced a slight distance beyond the soft tip 161 and imaging carried out in the manner hereinbefore described to ascertain the position of the distal extremity of the imaging guide wire 146 and at the same time to ascertain the position of the soft tip 161 of the outer sheath 143. If it is ascertained that the soft tip 161 is in the desired position so as to be able to make possible a penetration of the distal end cap 123, the inner sheath 144 carrying the sharpened distal extremity 221 serving as a needle cannula can be advanced by grasping the proximal extremity 217 and pushing it to cause it to slidably advance through the lumen 157 to push the sharpened tip 221 through the opening 163 at an angle to the longitudinal axis of the inner sheath 144 and through the perimeter of the distal fibrous end cap 123 while at the same time the imaging guide wire 146 is advanced to continuously ascertain the position of the distal extremity of the guide wire 146 which is coaxially mounted within the inner sheath 144 to thereby progressively monitor the positioning of the distal extremity 218 of the sheath 144 and thereby ascertain when the true lumen 103 has been reached as for example as shown in FIG. 8.

As soon as it has been ascertained that the tip of the imaging guide wire 146 is in the true lumen 103, the guide wire 147 can be removed along with the outer sheath 143 and the inner sheath 144, leaving the imaging guide wire 146 in place. As soon as this has been accomplished, the devices to be utilized for creating a flow passage through the stenosis 116 can be advanced over the imaging guide 146 as for example a balloon dilatation catheter until the balloon of the balloon dilatation catheter has been advanced through the stenosis 116 with the balloon being in the stenosis and past the distal end cap 123. As soon as this has been accomplished, the imaging guide wire 146 can be removed and the larger sized conventional guide wire 147 can be advanced through the balloon dilatation catheter so that it extends beyond the distal extremity of the balloon dilatation catheter and so that it is disposed within the lumen 103 of the vessel. In connection with the previous embodiment shown in FIG. 1, the balloon on the balloon dilatation catheter can now be inflated to compress the plaque 117 forming the stenosis 116 and to also increase the size of the openings through the proximal and distal caps 122 and 123 to provide a greatly increased flow passage through the stenosis 116 corresponding generally to the size of the lumen 103 t reestablish blood flow through the stenosis or lesion 116.

During the foregoing procedure, it should be appreciated that a contrast liquid can be introduced into the vessel during any of the procedures to facilitate observation fluoroscopically what is occurring during the procedure. As hereinbefore explained if larger size balloon dilatation catheters are desired to be utilized, the previous balloon dilatation catheter can be removed leaving the conventional larger size guide wire in place and thereafter advancing other devices as for example a larger size balloon dilatation catheter and thereafter inflating the balloon to create a still larger flow passage in the vessel. As hereinafter described it should be appreciated that if desired a stent can be deployed into the stenosis by the same or another catheter. Thereafter, the additional catheters can be removed followed by removal of the larger sized guide wire and the femoral artery closed in a conventional manner.

From the foregoing it can be seen that there has been provided a recanalization apparatus and method which is particularly efficacious for the treatment of total occlusions and more particularly chronic total occlusions to reestablish true lumens extending through the same. In this procedure and by the use of this apparatus it is possible to create true lumens without the danger of puncturing the vessel wall and which makes it possible to penetrate fibrous end caps which have convex surfaces facing in a proximal direction.

What is claimed:

1. A recanalization apparatus for use in crossing a stenosis forming a total occlusion in a vessel formed by a vessel wall, the stenosis having a distal end cap which is convex, facing in a proximal direction, comprising an outer sheath formed of an elongate flexible tubular member having proximal and distal extremities and having a lumen extending from the proximal extremity to the distal extremity, an inner sheath slidably mounted in the lumen of the outer sheath and being formed of an elongate flexible tubular member having proximal and distal extremities, the distal extremity of the elongate fleixble tubular member of the inner sheath having a sharp needle-like tip, the inner sheath having a length so that when the sharp needle-like tip is disposed distally of the distal extremity of the outer sheath, the proximal extremity extends proximally of the proximal extremity of the outer sheath and an imaging guide wire slidably mounted in a lumen of the inner sheath and having proximal and distal extremities and a transducer mounted on the distal extremity of the imaging guide wire, the imaging guide wire having a length so that the transducer can extend beyond the distal extremity of the inner sheath with the proximal of the imaging guide wire extremity extending proximally of the proximal extremity of the inner sheath.

2. Apparatus as in claim 1 wherein said outer sheath, said inner sheath and said imaging guide wire are coaxially mounted with respect to each other.

3. A recanalization apparatus for use in crossing a stenosis forming a total occlusion in a vessel formed by a vessel wall, the stenosis having a distal end cap which is convex, facing in a proximal direction, comprising an outer sheath formed of an elongate flexible tubular member having proximal and distal extremities and having a lumen extending from the proximal extremity to the distal extremity, an inner sheath slidably mounted in the lumen of the outer sheath and being formed of an elongate flexible tubular member having proximal and distal extremities, the distal extremity of the elongate fleixble tubular member of the inner sheath having a sharpened tip, the inner sheath having a length so that when the sharpened tip is disposed distally of the distal extremity of the outer sheath, the proximal extremity extends proximally of the proximal extremity of the outer sheath, an imaging guide wire slidably mounted in the lumen of the inner sheath and having proximal and distal extremities and a transducer mounted on the distal extremity of the imaging guide wire, the imaging guide wire having a length so that the transducer can extend beyond the distal extremity of the inner sheath with the proximal extremity of the energy guide wire extending proximally of the proximal extremity of the inner sheath, said outer sheath having first and second spaced-apart lumens, said inner sheath and said imaging guide wire being disposed in the first lumen and a conventional guide wire slidably mounted in the second lumen.

4. Apparatus as in claim 1 together with means connected to the proximal extremity of the imaging guide wire for supplying electrical energy to the transducer.

5. Apparatus as in claim 1 wherein said outer sheath has a shape memory element disposed in the distal extremity, said shape memory element having a predetermined bent shape when heated and means connected to the proximal extremity of the outer sheath for supplying heat to the shape memory element to cause bending of the distal extremity of the outer sheath.

6. Apparatus as in claim 1 together with means for introducing a flushing solution through the lumen of the outer sheath and through the lumen of the inner sheath.

7. A method for crossing a stenosis forming a total occlusion in a lumen in a vessel formed by a vessel wall, the distal extremity of the stenosis having an end cap which is convex facing in a proximal direction, by the use of an outer sheath having proximal and distal extremities and a lumen extending from the proximal extremity to the distal extremity, an inner sheath slidably mounted in the lumen in the outer sheath and having proximal and distal extremities and having a lumen extending from the proximal extremity to the distal extremity, the distal extremity of the inner sheath having a sharpened tip, the inner sheath having a length so that when its sharpened tip extends beyond the distal extremity of the outer sheath, the proximal extremity extends proximal of the proximal extremity of the outer sheath, an imaging guide wire slidably mounted in the lumen in the inner sheath and having proximal and distal extremities and having a transducer mounted on the distal extremity, the method comprising advancing the outer sheath so that its distal extremity is in the vicinity of the distal end cap so it engages the convex surface of the end cap and is deflected sideways in the vessel in a direction towards the wall of the vessel to form a false lumen, utilizing the imaging guide wire to image the wall of the vessel during the time that the outer sheath is being advanced to ascertain the position of the distal extremity of the outer sheath, to ascertain when the distal extremity of the inner sheath is facing in a direction which is toward the true lumen in the vessel, advancing the inner sheath to cause the sharpened tip to penetrate through the outer perimeter of the distal end cap and into the true lumen, withdrawing the inner sheath and the outer sheath while leaving the imaging guide wire in place and thereafter advancing at least one device over the imaging guide wire through the distal end cap and into the true lumen to perform additional procedures in the stenosis in the vessel.

8. A method as in claim 7 wherein the sharpened tip of the distal extremity of the inner sheath is advanced through the distal end cap at an angle with respect to the distal end cap.

9. A method as in claim 7 together with the step of withdrawing the imaging guide wire from the additional device after the at least one additional device has been advanced into the true lumen and thereafter inserting a conventional guide wire into the additional device and advancing it through the stenosis.

* * * * *